(12) United States Patent
Yang et al.

(10) Patent No.: US 8,331,097 B2
(45) Date of Patent: Dec. 11, 2012

(54) CLOTH COMPRISING SEPARABLE SENSITIVE AREAS

(76) Inventors: Chang-Ming Yang, Miaoli (TW); Tzulin Yang, Taipei (TW); Chingwen Yang, Taipei (TW); Hao Yang, Taipei (TW)

( * ) Notice: Subject to any disclaimer, the term of this patent is extended or adjusted under 35 U.S.C. 154(b) by 331 days.

(21) Appl. No.: 12/676,564

(22) PCT Filed: Sep. 3, 2008

(86) PCT No.: PCT/CN2008/001570
§ 371 (c)(1),
(2), (4) Date: May 6, 2010

(87) PCT Pub. No.: WO2009/033361
PCT Pub. Date: Mar. 19, 2009

(65) Prior Publication Data
US 2010/0296257 A1    Nov. 25, 2010

(30) Foreign Application Priority Data
Sep. 4, 2007  (WO) ................. PCT/CN2007/002649

(51) Int. Cl.
*H05K 1/00* (2006.01)
(52) U.S. Cl. ........ 361/749; 600/301; 600/383; 600/544; 473/199; 701/1; 701/29.1; 701/36; 701/37; 340/457.1; 340/573.1; 340/991
(58) Field of Classification Search ................. 361/749; 600/301, 383, 544; 473/199; 701/1, 29.1, 701/36, 37; 340/457.1, 573.1, 991
See application file for complete search history.

*Primary Examiner* — Xiaoliang Chen
(74) *Attorney, Agent, or Firm* — Osha Liang LLP

(57) ABSTRACT

A cloth material with separate conductive areas includes at least one first layer comprising at least one first conductive area; and at least one extension part, which includes at least one accessory and at least one connecting part connected to the accessory, wherein the extension part comprises at least one second conductive area, which corresponds in location to the first conductive area on the first layer, wherein the first conductive area and the second conductive area are inductively coupled, a condition of inductive coupling is adapted to be changed by an outside force.

18 Claims, 11 Drawing Sheets

CLOTH COMPRISING SEPARABLE SENSITIVE AREAS

CROSS REFERENCE TO RELATED APPLICATIONS

This is a national stage application of PCT/CN2008/001570, filed on Sep. 3, 2008, which claims priority of PCT/CN2007/002649, filed on Sep. 4, 2007. The disclosures of these prior filed applications are incorporated herein by reference in their entirety.

FIELD OF THE INVENTION

This invention relates to a type of cloth and leather material, especially materials having accessories and separate conductively sensitive areas that can change its condition when external force is applied

BACKGROUND

As we know, there are many technologies incorporating conductive material into cloth or leather material for making electrical circuits or to electronic components. Included here are some technologies that incorporate conductive material into cloth material for making electric switches. For example, a bendable switch is disclosed in U.S. Pat. No. 7,145,432, which makes use of a triple-layered textile material arranged in sequence to make an electric switch. Furthermore, U.S. Pat. No. 6,642,467 (corresponding to China Patent No. CN1252762C) discloses an electric switch that utilizes an upper layer and a lower layer of a conductive material sandwiching an elastic material. Included in it is a button component, which comprises a metallic ring and a piece of rope/thread that passes through the ring. The switch is operated by pulling on the rope/thread. It has 4 objects in all, and the rope is a non-conductive component. If it is to be in the form of a pressure sensor or a tension sensor, it needs to add a pressure-sensitive component, which is made of a Piezoelectric material, in order to produce an analog signal. Such a switch is easily damaged. The layered textile materials in the aforementioned electric switches are common and numerous. However, the manufacturing process using these materials is somewhat complicated.

Furthermore, U.S. Pat. No. 6,596,955 discloses devices having conductive materials fixed onto a zipper. The use of these is limited to cloths that have zippers. In addition, it can't be repaired by the user. In addition, China Patent No. CN1666308 discloses an electric switch made of an upper part and a lower part. However, because it is difficult to incorporate this into a cloth material, the manufacturing process is somewhat complicated.

In addition, some materials are used as signal or electric current transmitting devices, as disclosed in U.S. Pat. No. 7,154,071. Again, as in the above-described products, these devices have the disadvantages of requiring complicated manufacturing processes. U.S. Pat. Nos. 4,237,886 and 6,970,731, disclose snap-on button devices that can easily detach with prolonged use. U.S. Pat. No. 6,210,771 discloses a 2-part structure that can be used as a switch matrix. However, this switch not only easily gives a false signal, but its function is also easily affected by a wet cloth material caused by sweat or rain. Besides, this device can only measure pressure, but can't measure strain. For example, as disclosed in U.S. Pat. No. 7,210,939 (corresponding to China Patent CN1791337A), a button-hole interconnect is used as a conductor. This device includes an opening and a button interconnect; these two have to be operated manually by the user to be able to connect to the power source or an electronic equipment. Once electrically connected, it cannot be disconnected. Therefore, in terms of the environment and energy-saving, it is not ideal because it cannot automatically change its state of being conductive or non-conductive based on changes in outside forces. In addition, it can't distinguish the extent of conductivity once it is connected.

SUMMARY OF INVENTION

In view of the above-mentioned disadvantages, one of the objectives of this invention is to provide a type of cloth material with separate conductive areas that can be incorporated into a user's clothes or leather jacket. Therefore, the user can carry it around conveniently and it does not interfere with the user's motion.

Another objective of this invention is to provide a type of cloth material with separate conductive areas that can automatically cut off its power in the event that the textile layer gets wet.

Another objective of this invention is to provide a type of cloth material with separate conductive areas that can be used as a strain gauge or a pressure gauge for a user to measure strain or pressure.

Another objective of this invention is to provide a type of cloth material with separate conductive areas that can be used as a position change sensor gauge, a speedometer gauge, or accelerator gauge.

In addition, another objective of this invention is to provide a type of cloth material with separate conductive areas that can be used as an electrode.

Another objective of this invention is to provide a type of cloth material with separate conductive areas that can allow a user to easily replace defective parts when the system malfunctions.

Another objective of this invention is to provide a type of cloth material with separate conductive areas that can produce digital signals, because the resistance value is either very small or infinitely large, and the noise can be processed by a Schmitt trigger.

In order to achieve these objectives, this invention provides a type of cloth materials with separate conductive areas. A cloth material of the invention may include at least one first layer and at least one extension part; the first layer has a conductive sensor area and a non-conductive area located on the periphery of the first conductive area; the extension part is equipped with an accessory and a connecting part that connects with the accessory; a part of the accessory forms a second conductive area, the position of which corresponds to the first layer first conductive area. The first conductive area and the second conductive area are inductively connected (coupled). The inductive coupling conditions can change with an external force. Based on this, when an external force is applied, the first conductive area may come into contact with the second conductive area to form an electrically-conductive path. When the external force disappears, the system will revert to its original condition. Cloth materials of the invention may be incorporated into user's clothes or leather jackets. Therefore, a user can carry it around conveniently and it does not interfere with the user's motion.

Based on the above technical aspects, cloth materials with separate conductive areas in accordance with the invention have at least the following advantages and beneficial effects:

1) This invention's cloth materials with separate conductive areas may be used as an accessory to clothing apparel. If broken, such an accessory can be removed.

When not in use, the accessory can be removed as a whole unit. The extent of use is only limited, hence, it is simple and easy to use;

2) The digital signal is either 0 or 1, hence energy efficient;

3) This invention's cloth materials with separate conductive areas may use conventional clothing materials that look like ordinary clothing and not extravagant. It is washable and not easily destroyed;

4) Basically, one component may have several functions, e.g., as a switch, electrode, pressure sensor, or signal transducer.

The above explanation is only a brief summary of the technical aspects of the invention. In order to further understand these and other objectives and technical aspects of the invention, and for one to practice the invention based on the description, we provide the following preferred examples with accompanying drawings:

BRIEF DESCRIPTION OF DRAWINGS

In order to appreciate further the structure and special features of this invention, we hereby describe the following preferred examples with accompanying figures.

Figure 1:
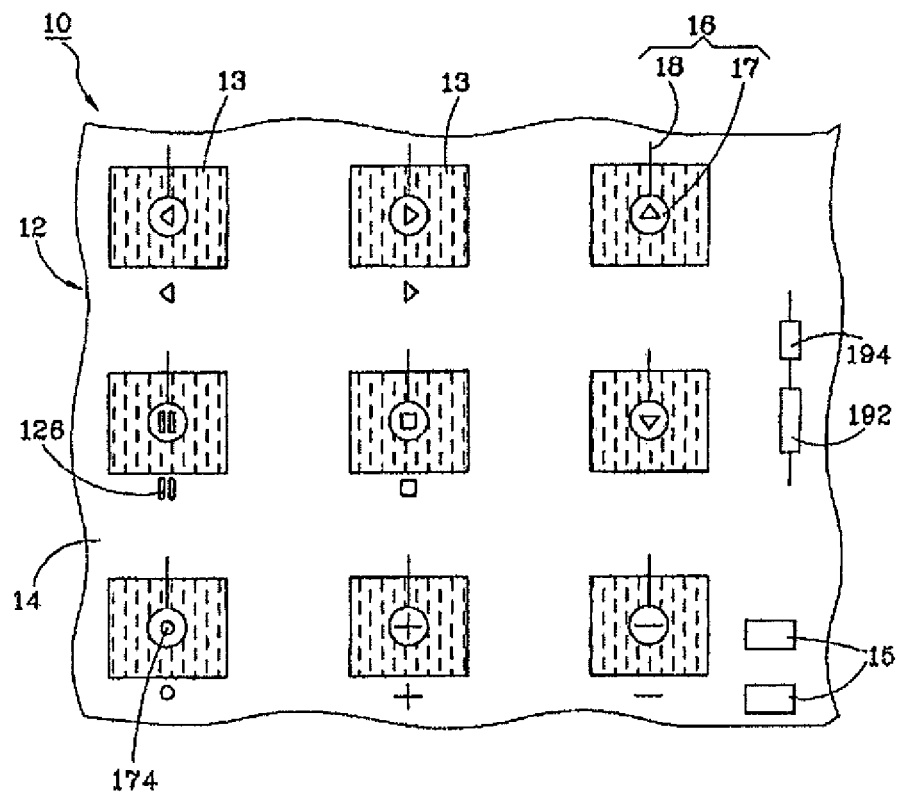
FIG. 1 shows a front view of this invention's first preferred example.

10 cloth material with separate conductive areas

12 First layer 126 Diagram 13 First conductive area

14 Non-conductive area 15 Reference area 16 Extension part

17 Accessory 172 Second conductive area 174 Diagram

18 Connecting part 192 Control circuit 194 Output device

10$a$ cloth material with separate conductive areas

12$a$ First layer 13$a$ First conductive area 14$a$ Non-conductive area

16$a$ Extension part 17$a$ Accessory 172$a$ Second conductive area

18$a$ Connecting part

10$b$ cloth material with separate conductive areas

12$b$ First layer 121$b$ Fillister 13$b$ First conductive area

14$b$ Non-conductive area 16$b$ Extension part 17$b$ Accessory

172$b$ Second conductive area 18$b$ Connecting part

192$b$ Control circuit

194$b$ Output device

10$c$ cloth material with separate conductive areas

12$c$ First layer 121$c$ Fillister 13$c$ First conductive area

14$c$ Non-conductive area 16$c$ Extension part 17$c$ Accessory

172$c$ Second conductive area 18$c$ Connecting part

10$d$ cloth material with separate conductive areas

12$d$ First layer 123$d$ Convexity 13$d$ First conductive area

14$d$ Non-conductive area 16$d$ Extension part 17$d$ Accessory

172$d$ Second conductive area 174$d$ Convexity 18$d$ Connecting part

10$e$ cloth material with separate conductive areas

12$e$ First layer 121$e$ Fillister 13$e$ First conductive area

14$e$ Non-conductive area 16$e$ Extension part 17$e$ Accessory

172$e$ Second conductive area 18$e$ Connecting part

192$e$ Control circuit

194$e$ Output device

10$f$ cloth material with separate conductive areas

12$f$ First layer 125$f$ Perforation 13$f$ First conductive area

14$f$ Non-conductive area 16$f$ Extension part 17$f$ Accessory

172$f$ Second conductive area 18$f$ Connecting part

10$g$ cloth material equipped with separate conductive areas

12$g$ First layer 13$g$ First conductive area 14$g$ Non-conductive area

16$g$ Extension part 17$g$ Accessory 172$g$ Second conductive area

18$g$ Connecting part 192$g$ Control circuit

194$g$ Output device

10$h$ cloth material with separate conductive areas

12$h$ First layer 125$h$ Perforation 13$h$ First conductive area

14$h$ Non-conductive area 16$h$ Extension part 17$h$ Accessory

172$h$ Second conductive area 18$h$ Connecting part

10$k$ cloth material with separate conductive areas

12$k$ First layer 125$k$ Perforation 13$k$ First conductive area

15k Non-conductive area 16k Extension part 17k Accessory
(Second conductive area) 18k Connecting part
20 cloth material with separate conductive areas
22 First layer 23 First conductive area 24 Non-conductive area
25 Extension part 26 Accessory 262 Second conductive area
27 Connecting part 28 Enhancing wire 29 Second layer
30 cloth material with separate conductive areas
32 First layer 33 First conductive area 34 Non-conductive area
35 Extension part 36 Accessory 362 Second conductive area
37 Connecting part 39 Second layer
40 cloth material with separate conductive areas
42 First layer 421 Perforation 43 First conductive area (conductible fine wire) 44 Non-conductive area
45 Extension part 46 Accessory (button) 47 Second conductive area
(connecting part) 49 Second layer
50 cloth material with separate conductive areas
52 First layer 521 Perforation 53 First conductive area
54 Non-conductive area 55 Extension part 56 Accessory (Second conductive area) 561 Electronic component
57 Connecting part 59 Second layer
60 cloth material with separate conductive areas
62 First layer 621 Perforation 63 First conductive area
64 Non-conductive area 65 Extension part 66 Accessory (Second conductive area) 661 Electronic component
67 Connecting part 68 Header 69 Second layer
70 cloth material with separate conductive areas
72 First layer 721 Perforation 73 First conductive area
74 Non-conductive area 75 Extension part 76 Accessory
77 Connecting part 79 Second layer
80 cloth material with separate conductive areas
81 First conductive area
82 Second layer 83 Ring button
84 Non-conductive area 88 Accessory (second conductive area)
89 First layer
90 cloth material with separate conductive areas
92 First layer 921 Female snap-on button 93 First conductive area (conductive fine wire)
94 Non-conductive area 95 Extension part 96 Accessory (female snap-on button) 97 Connecting part (second conductive area)
99 Second layer
90a cloth material with separate conductive areas
92a First layer 93a First conductive area (clip hook) 94a Non-conductive area
95a Extension part 96a Accessory (second conductive area)
97a Connecting part 99a Second layer
11 cloth material with separate conductive areas
112 First layer 113 First conductive area
114 Non-conductive area
115 Extension part 116 Accessory 1162 Second conductive area
117 Connecting part 118 Channel 119 Second layer

DETAILED DESCRIPTION

In order to further explain this invention's technological methods used and its effects, the following preferred examples with accompanying drawings are presented. The following description is provided to answer the questions regarding this invention's cloth materials with separate sensor areas with regards to their application methods, structure, special qualities and effectiveness.

Figure 2:
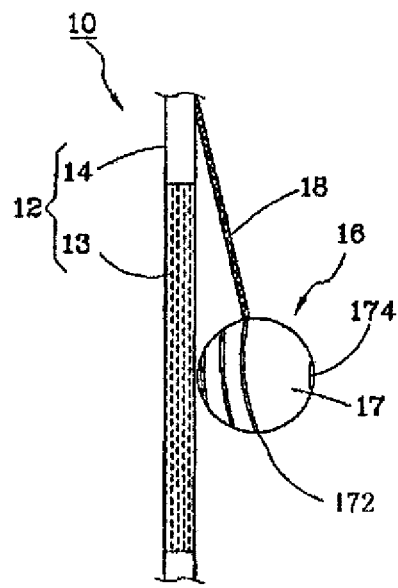
FIG. 2 shows a side view of the detailed structure of this invention's first preferred example.

Please refer to FIGS. 1 and 2: this invention's first preferred example that provides a type of cloth material 10 with separate sensor areas includes one first layer 12, several extension parts 16, one electrical control circuit 192, and one output device 194.

On top of the first layer 12 includes several first sensor areas 13, one non-sensor area 14, and two reference areas 15. The first sensor areas 13 and the reference area 15 are both conductive. The first sensor areas 13 is arranged in a matrix and penetrates the first layer 12. The non-sensor area 14 is located between and around the first sensor areas 13, and can be made of a non-conductive, non-magnetic textile fiber material or leather. The reference area 15 is far away from the first sensor areas 13. The first sensor areas 13 and the reference area 15 can be formed in the following manner (but not limited to it):

1. By means of a single textile process, weaving non-conductive fibers and conductive fibers together, either by knitting, weaving, tatting, embroidering, or other appropriate means;
2. By means of embedding, sticking or weaving a conductive metallic plate into the first layer 12;
3. By means of sewing fine, conductive wires into the first layer 12;
4. By means of applying a conductive material with an adhesive substance over the first layer 12.
5. By means of sticking or sewing a conductive cloth material over the first layer 12.

The above-mentioned non-conductive textile fibers may include, but not limited to, cotton, hemp or nylon, while the conductive fibers may include polymer conductive fibers or conductive metallic fibers, or weaving a stainless steel fiber and a non-conductive fiber together, or applying a conductive substance over a non-conductive fiber. The percentage of the conductive fibers in the first sensor areas 13 can account for from 1% to 100%.

The extension parts 16 each contain an accessory 17 and a connecting part 18. This accessory 17 may be spherical in shape, pillar-shaped, polygon-shaped or saucer-shaped, is elastic, and can change shape due to pressure and revert to its original shape if the external force disappears. It can be made of rubber, foam, sponge, spring, cotton, spandex, lycra, SBR (Styrene Butadiene Rubber), or foam-based material. On the surface of any of the accessories 17, there may be three circular second sensor areas 172. Each circle represents a resistance value. These second sensor areas 172 are made of a conductive material and may be formed in a similar fashion as the afore-mentioned first sensor areas 13, such as: 1, sewing together non-conducting fibers and conducting fibers into an accessory component 17 using a textile process, for example knitting, weaving, or other appropriate process; 2, Embedding, sticking, or sewing conductive metal plates into the accessory 17; 3, Sewing conductive fine wires into the accessory 17; 4, Applying or sticking conductive materials on the accessory 17; 5, Sticking, sewing or gluing an already conductive cloth material onto the accessory 17. The location of the second sensor area 172 corresponds to the location of the first sensor area 13 in the first layer 12. The connecting part 18 in this example is made of 3 interconnected conductive fine wires and another thick wire woven together. One end of the connecting part 18 is connected with the accessory 17, and the other end is connected with the non-sensor area 14 of the first layer 12. The accessory itself may contain high-density material, like metal or glass, which will cause it to hang downward. The connecting art 18 of the extension part 16 is electrically connected to the corresponding second sensor areas 172. The extension part 16 is separated from the reference area 15 of the first layer 12. In addition, the accessory 17 may be a button, shiny disc, or a pearl similar to accessories used on modern garments. The accessory 17 may also contain high-density material, like metal or glass, which will cause it to hang downward.

The control circuit 192 may be removably fixed on the first layer 12. It may be a printed circuit board or an IC board with an integrated power source. The control circuit 192 is electrically connected to the first sensor areas 13 and the reference area 15 on the first layer 12. It is also electrically connected to second sensor areas 172 of the accessory 17 via the connecting art 18. Based on the above, when a user applies pressure on the accessory 17 pushing it towards the first layer 12, the second sensor areas 172 of the accessory 17 may come into contact with the corresponding first sensor areas 13, thereby forming a circuit among the first sensor areas 13, second sensor areas 172, and the control circuit 192.

The output device 194 is electrically connected to the control circuit 192, and is a device that can send signals wirelessly. When a user applies pressure on the accessories in different locations, the control circuit 192 will command the output device 194 to send different signals based on the different locations of the accessories where pressure has been applied. The output device 194 and control circuit 192 may also be fixed on the accessory.

Furthermore, the control circuit 192 may include a resistance-multiplexed switches which can be used to measure the resistance in the circuit. When the user applies an increasing amount of pressure, the accessory 17 may change shape accordingly, causing more and more of its second conductive areas 172 to contact the first sensor areas 13. At this time the resistance in the circuit will become smaller. Such a system can function as a pressure gauge. The control circuit 192 may be programmed with a resistance threshold value. When it detects a resistance lower than the threshold, the control circuit 192 will command the output device 194 to send a signal. Otherwise, if the resistance is higher than the threshold, the control circuit 192 will not issue a command, thereby preventing accidentally triggering the system.

Furthermore, the second sensor areas 172 may be designed to have three insulated conductive wires that are independently connected to the control circuit 192. Therefore, when the three second sensor areas 172 on the accessory 17 come into contact with the first sensor area 13, the first sensor area 13 and the second sensor areas 172 can produce three different signals to the control circuit 192. In addition, depending on the amount of pressure exerted by the user, the number of conductive loops (circuits) formed on the cloth material 10 will vary. Hence, the cloth material with separate sensor areas 10 may be used as three-stage switches. Each stage of the switches can represent different amounts of external force applied. This can show three sets of digital signals rather than analog signals, thereby doing away with complicated signal processing, and also avoiding the need for an AD converter. At the same time, this can detect force directionality: the accessory 17 is pressed against the cloth material 10 to have a response. If the cloth material 10 is pressed towards the accessory 17, there will be no response. Because behind the cloth material 10 is a user's body, this will greatly decrease the possibility of false signals.

The two reference areas 15 on the first layer 12 is spaced apart, and they are also separated from the first sensor areas 13 on the first layer 12 and from the extension part 16. Therefore, when the cloth material 10 is used normally, the two reference areas 15 would not form a loop (circuit), neither will any of the two reference areas 15 come into contact and form a loop with the first or second sensor areas 13, 172. Nevertheless, if the two reference areas 15 form a loop, or either of the two reference areas 15 forms a loop with either the first sensor areas 13 or the second sensor areas 172, the control circuit 192 will immediately cut off power to prevent short-circuit, causing electrical skock to the user. At the same time, the control circuit can also command the output device 194 to send an alarm signal to notify the user. Similarly, when the first sensor areas 13 on the first layer 12 form a loop among themselves, or the second sensor areas 172 of the extension part 16 form a loop among themselves, or if the cloth material 10 changes its condition when external force is applied, gets wet or loses its function, the control circuit 192 may cut off the power, and at the same time may act as a wetness indicator gauge.

Based on the above-mentioned structure, the cloth material 10 with separate sensor areas can be made into a piece of clothing for the user to wear, or into a remote control device. The user can press on the accessories 17 at different locations, or on the same accessory to contact different sensor areas 13, to activate the output device 194 to send different signals wirelessly to switch channels on a TV set, control the sound volume, or set the thermostat control of an air-conditioner. Aside from these, the first layer 12 and the accessory 17 both may have diagrams 126, 174 (see FIGS. 1 and 2) to illustrate these functions. Because a cloth material 10 with separate sensor areas may be designed to be incorporated into a cloth or leather worn by a user, it would be convenient for the user to carry around without affecting the user's motions.

In addition, the first layer 12 can be made into a piece of underwear, placing the extension part 16 on the outer side of the first layer 12. By means of pressing on the accessories 17 at different locations, it will cause the first sensor areas 13 at different locations or reference areas 15 to come in contact with the site to be tested on the user's skin. Based on this, the first sensor areas 13 can be used as an electrode for EKG, respiration, EMG, EEG, "Transcutaneous Electrical Nerve Stimulation" (TENS) device, or defibrillator. Also, the cloth material 10 with separate conductive areas can be used to provide electric current for an electric clothing to the user warm. In another word, the cloth material 10 with separate conductive areas can be used to transmit not only physiological signals from the user, but also electric current or signals from outside to the user, making it a device for transmitting signals and electric current. This device may be activated only when external force is applied to the first conductive areas and the second conductive areas 172, such as when a clothe is worn by a user, and may automatically turn off when no external force is applied, such as when a clothe is removed by the user. Therefore, there is no need for the user to constantly turning on and off a switch. Such a device may also transmit multiple signals and electric currents.

Furthermore, the cloth material 10 with separate conductive areas may be placed around arm pit, enabling a user to establish electrical conduction simply by pressing his upper arm against the side of his chest. Furthermore, the output device 194 can be an LED, an electric horn or a slim monitor panel, which can emit light, sound or show the pressed location based on electric conductance.

In addition, when the cloth material 10 with separate conductive areas is made into an upper body clothing and worn by the user, by analyzing electric conductance between the first and second conductive areas 13, 172 at different locations of the user's body, one can ascertain the actions of the user. For example, by knowing that the first and second conductive areas 13, 172 on the anterior chest of the user are not in contact and that the first and second conductive areas 13, 172 on the back of the user are in contact with one another, we can ascertain that the user is bending down. Or, when the second conductive areas are in electrical contact with the non-corresponding first conductive areas, one can assume that the user is turning (twisting) his body. When the user turns to the right, the accessory may rotate to the left, coming into contact with a conductive area on the left side. Based on this, the cloth material 10 with separate conductive areas can be used as a testing device for detecting changes in the user's position, such as to detect falling down.

Due to the fact that the magnitude of electrical resistance in a loop is affected by the amount of pressure exerted on the accessory 17, the cloth material 10 with separate conductive areas can be used as a resistance-multiplexed switches or a pressure gauge. For example, if used as a sole in a shoe, the multiple pressure transducers would allow one to know the changes in a user's gait or foot pressures in different areas.

Furthermore, the cloth material 10 with separate conductive areas can be used as a switch matrix or a keyboard. That is, based on the level of the loop's resistance, the "ON" and the "OFF" switches can be formed. Also, when the user presses on the accessory 17, the accessory 17 may change shapes under pressure, thereby allowing the user to know for certain that the accessory 17 has indeed been pressed. And when the user releases his finger from the accessory 17, the user can feel that the accessory 17 has returned to its original shape due to its elasticity. In addition, the cloth material 10 with separate conductive areas can also be designed to have a single first conductive area 13 or a single extension part 16 and used as a single electric switch. A single extension part 16 may also be used with four first conductive areas, namely on the upper, lower, right and left, which can be used as a multi-staged electronic switch. In addition, whether the switch is ON or OFF may be determined by whether the amount of pressure applied exceeds a threshold. Using the same principle, we can design it to be a simple ON/OFF switch. Unlike a traditional accelerometers or gyroscope sensor that are too sensitive and cannot be worn or washed as a piece of clothing, a device of the invention can be worn or washed. When we use this as a gait analyzer or a long-term position change monitor, using wired or wireless means to send the signals of the various body positions as an ON/OFF signal (i.e., 0 or 1) to a care-taker, the care-taker will be able to monitor the present conditions of a user, such as whether the user has fallen, is in epileptic seizure, has suffered a stroke, or has any abnormal changes. At the same time, the 0,1 signals can be converted into 3D animations. If the user has suffered a stroke, we can use this gait analyzer or position change monitor to facilitate rehabilitation. At the same time, medical personnel can monitor the progress of the user. If the user is a healthy person, it can be used as an exercise guide, as in the tai-chi, where harmony between breathing and movement are emphasized. The ordinary person does not realize this, but if this sensor is used to monitor breathing and position, using 3D animation, it will show the changes in breathing which will be easy for the beginner to understand. The above examples show that the signals are all digital, not analog.

Figure 3:
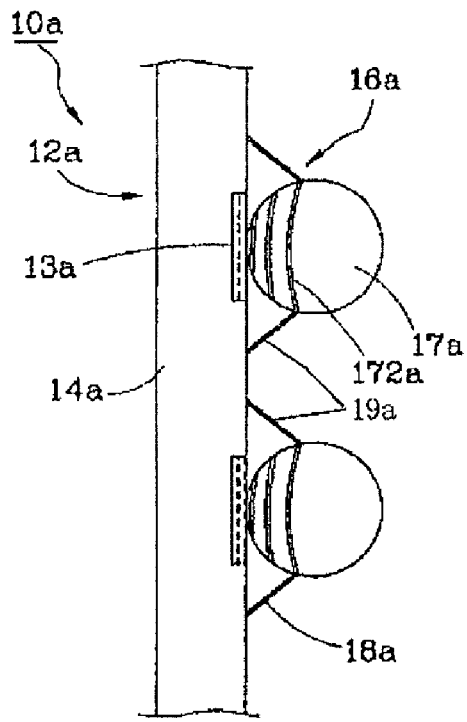
FIG. 3 shows a side view of this invention's second preferred example.

The structure of the cloth material 10 with separate conductive areas can also be variable. Please refer to FIG. 3: a cloth material 10a with separate conductive areas provided in this invention's second preferred example is almost the same as that of the previous example. The only difference is that the first conductive areas 13a on the first layer 12a form only on the surface of the first layer 12a, and not penetrating the first layer 12a. Each of the extension parts 16a all includes 2 connecting parts 18a connected to the accessory 17a and the first layer 12a, making it easy to fix the accessory 17a in a specific location. The accessory 17a is made of an elastic material, while the cloth material may be a stretchable, woven cloth material, such as an elastic band. The extension parts 16a may include a non-conductive reinforcing thread 19a, connected to accessory 17a, enabling the accessory 17a to be stably fixed at a specific location. The reinforcing thread may include elastic material and is stretchable.

Since the first and the second conductive areas 13a, 172a are formed between the first layer 12a and the accessory 17a, it can prevent short-circuit of the cloth layer 10a when the first layer 12a is folded or twisted. Furthermore, the accessory 17a can be made of a hard material, which can resist deformation, thereby maintaining a constant resistance in the electrical loop. Hence, the cloth material with separate conductive areas 10a can be used as a passive resistor. Such a cloth material 10a can be used as passive resistance components.

In addition, the accessory 17a may be made of an elastic material. Therefore, when a user stretches the first layer 12a, due to the tension of the connecting wire 18a, the accessory 17a will intimately contact the first electric conductance areas 13a, resulting in a change in the resistance of the loop. Since the value of the resistance depends on the amount of pressure exerted by the user, hence the cloth material 10a with separate conductive areas can also be used as a strain gauge.

Furthermore, the cloth material 10a with separate conductive areas can also be made into a piece of clothing to be worn by a user. Due to the user's inhalation, exhalation, swallowing, or other body movements, the strain that is made to bear on the cloth material 10a can change. Therefore, this cloth material 10a can also be used as a position change sensor, a breathing sensor or a swallow sensor.

In addition, the two threads need not be separately attached to the accessory 17a. Instead, these may comprise a single connecting part 18a passing through the accessory 17a. In this case, the accessory 17a has a channel that allows the connecting part 18a to pass through. When external force or pressure is applied, the accessory 17a may move/slide freely, whether it comes into contact with the first conductible area 13a or not. With this embodiment, one can detect the relative change in position, relative change in movement speed, and relative change in acceleration between the accessory 17a and the first conductible area 13a.

Figure 4:
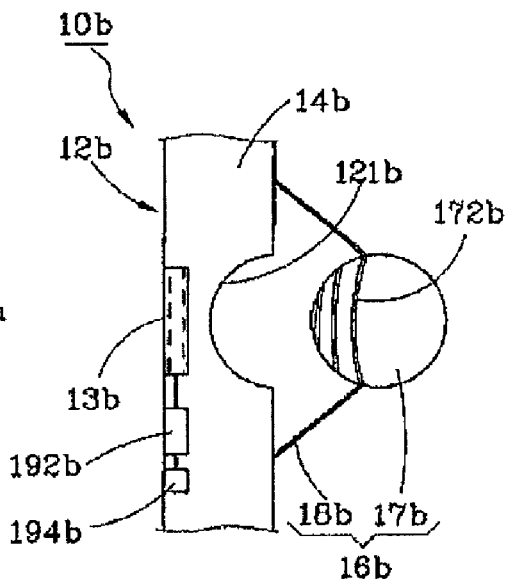
FIG. 4 shows a side view of this invention's third preferred example.

Furthermore, as shown in FIG. 4, on one side of the first layer 12b forms a fillister (trough) 121b to accommodate the accessory 17b. The first conductive area 13b forms on the first layer 12b on the side opposite to the side facing the accessory 17b, and location of the first conductive area 13b corresponds to the fillister 121b. Both the first and second conductive areas 13b, 172b can conduct electricity. Therefore, they can form a capacitor. The control circuit 192b may include a capacitance meter for measuring the capacitance of the first and second conductive areas 13b, 172b. Based on this, the control circuit 192b can trigger the output device 194b to send signals based on the capacitance levels as determined by the changes in distances between the first and second sensor areas 13b, 172b.

In addition, because the accessory 17b may be located in the fillister 121, it can effectively prevent the user from mistakenly touching the second sensor areas 172b of the accessory 17b.

When the relative positions of the first and second sensor areas 13b, 172b are fixed, the cloth material 10b can also be used as passive capacitance material with a fixed (stable) capacitance. Also, one can change the surface areas or the space between the first and second conductive areas 13b, 172b to design different passive capacitance materials with different capacitance levels. For example, accessory 17b may include an insulator layer to increase the distance between the first and second conductive areas and to affect the capacitance. When the positions and shapes of the first and second conductive areas 13b, 172b are changable, the cloth material 10b can also be used as variable capacitors. In addition, because the change in capacitance is related to the distance between the first and second conductive areas 13b, 172b, one can analyze the change in the capacitance to learn the speed or acceleration of the accessory 17b relative to the first conductive area. Therefore, the cloth material 10b can also be used as a position change detector, speedometer or an acceleration detector. For example, when this cloth material is used in a shoe, it can be used to analyze thae user's gait and detect whether the user has fallen down.

Figure 5:
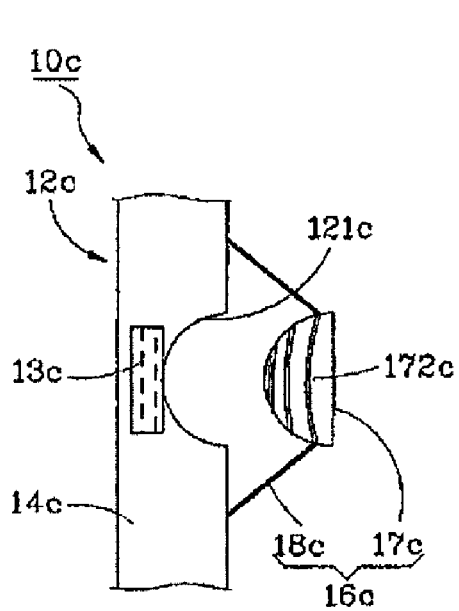
FIG. 5 shows a side view of this invention's fourth preferred example.

Referring to FIG. 5, one can design the size of the extension part 16c and the accessory 17c so that they correspond to the fillister 121c of the first layer 12c. Based on this, when the accessory 17c completely fits into the fillister 121c, the surface of the cloth material 10c with separate conductive areas is maintained in a level position to increase its aesthetic value. In addition, the first conductive area 13c of the first layer 12c may be located inside the first layer 12c. The surface of the cloth material 10c need not be flat; it can be a pile, fleece, or other compressible cloth material. The first conductive area 13c may be located on the bottom layer of the cloth material and forms a fillister. The accessory 17c may be located on the surface of the cloth material 10c. When an external force is applied, the cloth material 10c is compressed, causing the first conductive area 13c to come into close to the second conductive area 172c; when external force disappears, it reverts to its original condition. Behind the accessory 17c may be a user's body. Therefore, when the direction of the force applied is from the cloth material 10c towards the accessory 17c, the reaction produced may be large, and when the direction is from the accessory 17c towards the cloth material 10c, the reaction may be small. Hence, the directions of the force applied can be distinguished.

Figure 6:
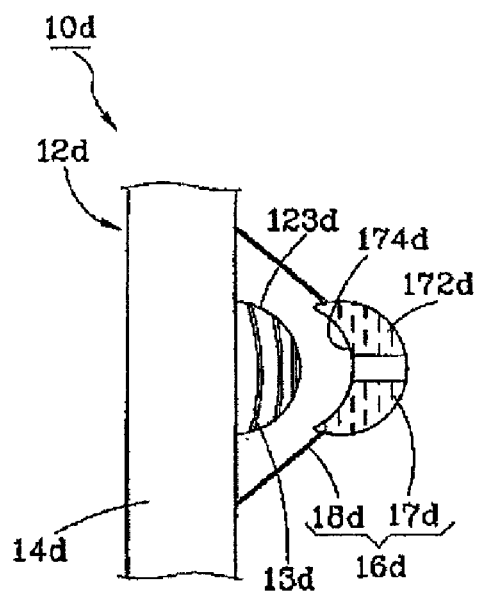
FIG. 6 shows a side view of this invention's fifth preferred example.

Please refer to FIG. 6, the cloth material 10d with separate conductive areas provided in this invention's fifth preferred example is almost the same as that of the previous example. The only difference is that on top of its first layer 12d is a convexity (bump) 123d. The first layer 12d may have many ring-shaped first conductive areas 13d forming on top of the convexity 123d. Its accessory 17d has 2 second conductive areas 172d which are made of a conductible material. The accessory 17d also has a concavity 174b which can accommodate the convexity 123d. Based on mutual contact between the first and second conductive areas 13b, 172b on different locations, the first and second conductive areas 13b, 172b can produce different signals to the control circuit. The cloth material 10d may be compressible. Its material can be rubber, vesicating material, sponge, spring, cotton, spandex, lycra, SBR (Styrene Butadiene Rubber), and foam-based material. The first conductive area of the first layer 12d does not need to be protruding, but may be flat. When external force is applied, the cloth material 10d is compressed, causing the first conductive area 13c to come into contact with the second conductive area 172c; when external force disappears, it reverts to its original condition.

Figure 7:
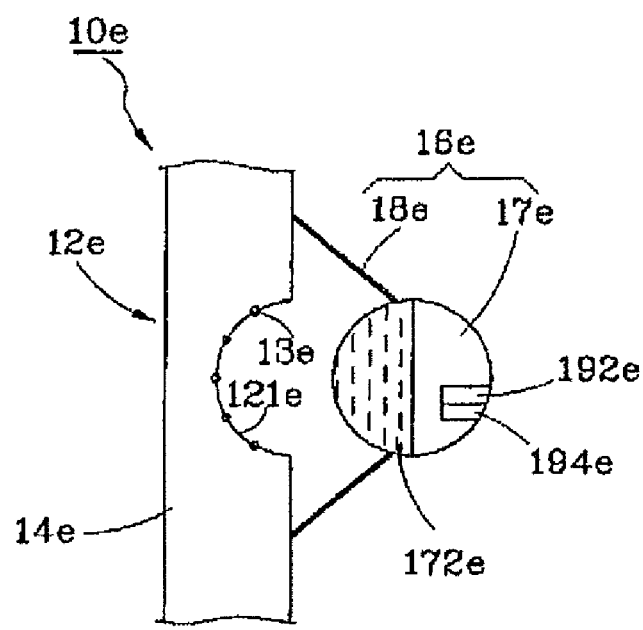
FIG. 7 shows a side view of this invention's sixth preferred example.

Please refer to FIG. 7, the cloth material 10e with separate conductive areas provided in this invention's sixth preferred example is almost the same as that of the previous example. The only difference is that the first conductive area 13e of the first layer 12e is located on the inner sidewall of the fillister 121e, and may contain several independent conductive areas (here it contains three conductive areas). The second conductive area 172e of the accessory 17e is dome-shaped. The control circuit 192e and the output device 194e are located on top of the accessory 17e, and they are connected to the first conductive area 13e via the connecting wire 18e. The accessory 17e contains only one conductive area 172, whereas the cloth material 13e contains three independent conductive areas.

Figure 8:
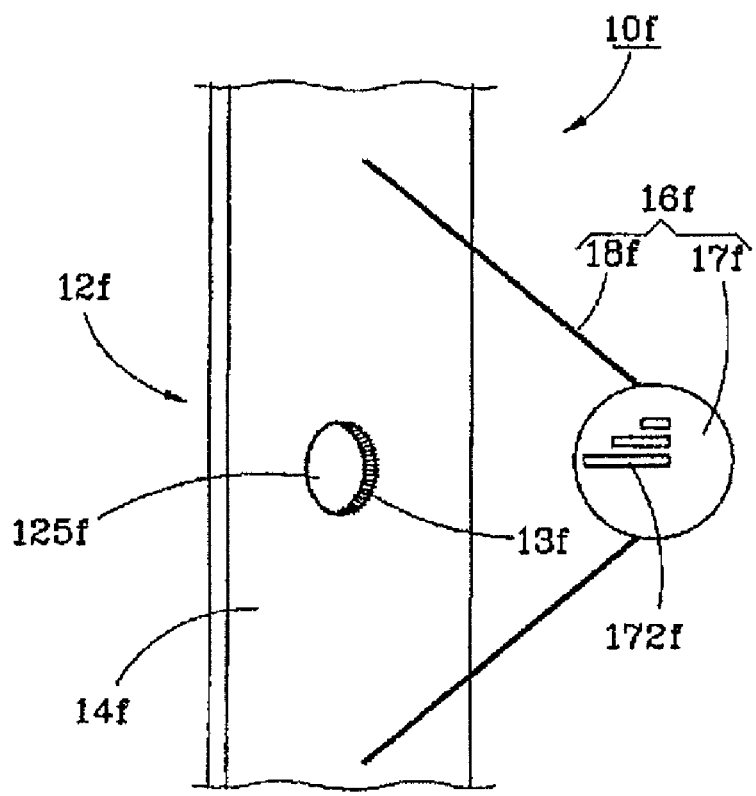
FIG. 8 shows a 3-D view of this invention's seventh preferred example.

Please refer to FIG. 8, the cloth material 10f with separate conductive areas provided in this invention's seventh preferred example is almost the same as that of the previous example. The only difference is that there is a perforation 125f on its first layer 12f. The first conductive area 13f of the first layer 12f is formed by sewing fine conductible wires around the perforation 12f. The first layer 12f includes elastic material, for example elastic fibers or rubber. Therefore, the perforation 125f can be stretched, and the bigger the external force, the bigger is the diameter of the opening. The second conductive area 172f of the accessory 17f is shaped like strands, and is formed by sewing fine conductive wires on the accessory 17f. The more the area of contact, the larger the external force is. The larger the diameter of the opening 125f is, the more contact area is between the first and second conductive areas 13f and 172f. Therefore, this can be used as a pressure sensor or a strain sensor. The connecting part may be made of an elastic material, and through its elasticity we can increase its sensitivity.

Figure 9:
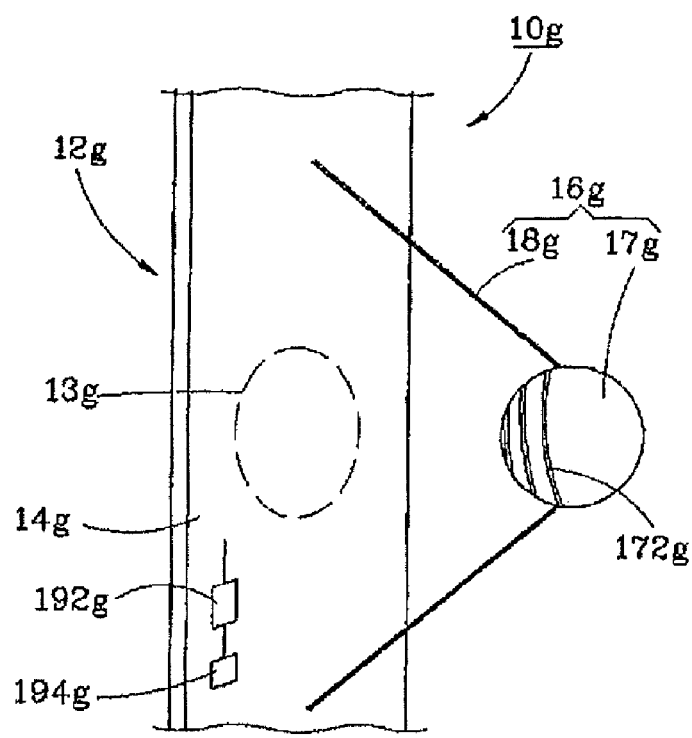
FIG. 9 shows a 3D view of this invention's eighth preferred example.

Please refer to FIG. 9, the cloth material 10g with separate sensor areas provided in this invention's eighth preferred example includes a first layer 12g, an extension part 16g, a control circuit 192g, and an output device 194g. The first conductive area 13g of the first layer 12g is ring-shaped. The extension part 16g includes an accessory 17g and a connecting wire 18g which connects the accessory 17g and the non-conductive area 14g of the first layer 12g. The second conductive area 172g of the accessory 17g is made of a magnetic material. The connecting wire 18g is non-conductive. Based on this, when the accessory 17g comes near or goes far from the first layer 12g, the second conductive area 172g of the accessory 17g can cause the ring-shaped first conductive area 13g to produce a reactive electromotive force. The control circuit 192g can detect the reactive electromotive force, and can command the output device 194g to send signals based on it. In another word, the cloth material 10g with separate conductive areas can be used as a passive inductance material.

Figure 10:
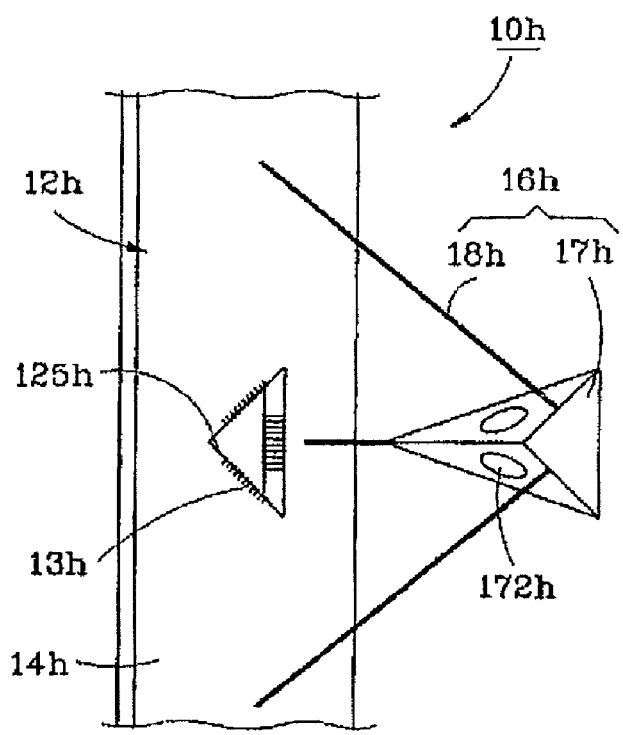
FIG. 10 shows a 3D view of this invention's ninth preferred example.

Please refer to FIG. 10, the cloth material 10g with separate conductive areas provided in this invention's ninth preferred example is almost the same as that of the previous example. The only difference is that the perforation 125h on its first layer 12h is triangle-shaped. The cloth material 10g may have 3 first conductive areas 13h forming individually on the 3 sides of the perforation 125h. The accessory 17h forms a pyramid, and has 3 second conductive areas 172h forming individually on the 3 sides of the accessory 17h. The number of the connecting wires 18h is 3 as well. The accessory 17h of the pyramid can allow the user to conveniently slip it into the perforation 125h. One can design the perforation 125h to be smaller in size to increase the market acceptance of the cloth material 10h. One can have one or more electric current or signal transmitting devices. The connecting part may be composed of an elastic material. So, when the accessory 17h is pushed into the perforation 125h, the influence exerted by the external force on the two is minimal.

Furthermore, due to the fact that the perforation 125h and the accessory 17h are non-rounded, they can guide a user to first rotate the accessory 17h to an appropriate angle before inserting it into the perforation 125h, so that the second conductive area 172h can more accurately contact the first conductive area 13. Therefore, a single accessory can have many different conductive areas that interact with the different conductive regions in the first conductive areas of the cloth material 10*h*.

Figure 11:
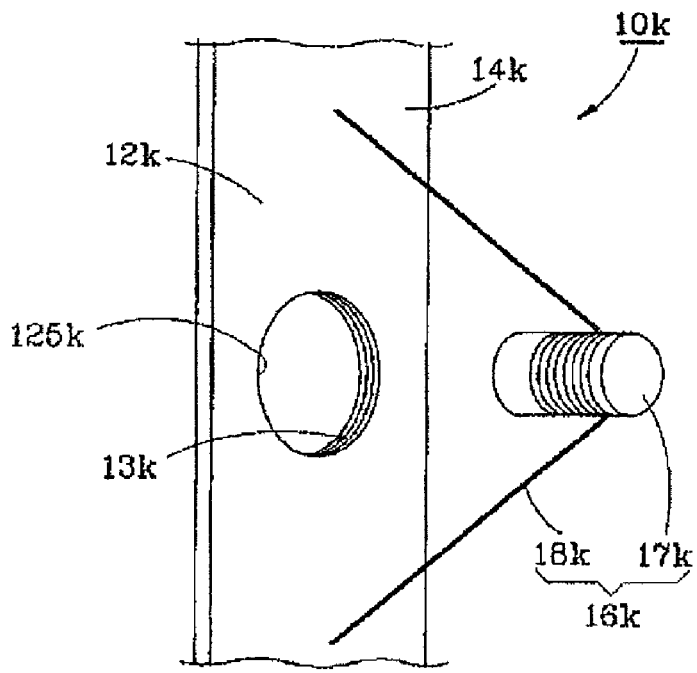
FIG. 11 shows a 3D view of this invention's tenth preferred example.

Please refer to FIG. 11. A cloth material 10*k* with separate conductive areas provided in this invention's tenth preferred example is almost the same as that of the previous example. The only difference is that the first conductive area 13*k* of the first layer 12*k* is formed by sewing conductible fine wires along the perforation 125*k* in a winding, helical pattern. The accessory 17*k* of the extension part 16*k* is made of a magnetic material, which forms the second conductive areas 17*k*. The accessory 17*k* is cylindrical in shape. The connecting wire 18*k* of the extension part 16*k* is made of a metallic material, and winds around the accessory 17*k* helically like a coiled spring. Based on this, when there is electric current flowing in the connecting wire 18*k*, and when the accessory 17*k* is far away from or near the perforation 125*k*, the accessory 17*k* will cause the first conductive area 13*k* to produce a reactive electromotive force. Since the accessory 17*k* is cylindrical in shape, it is easy to design and manufacture. Because the accessory has the special characteristics of a coiled spring, when the external force disappears, it still oscillates several times, transforming kinetic energy (such as energy from exercise) into electrical energy and stores it.

Figures 12, 13:
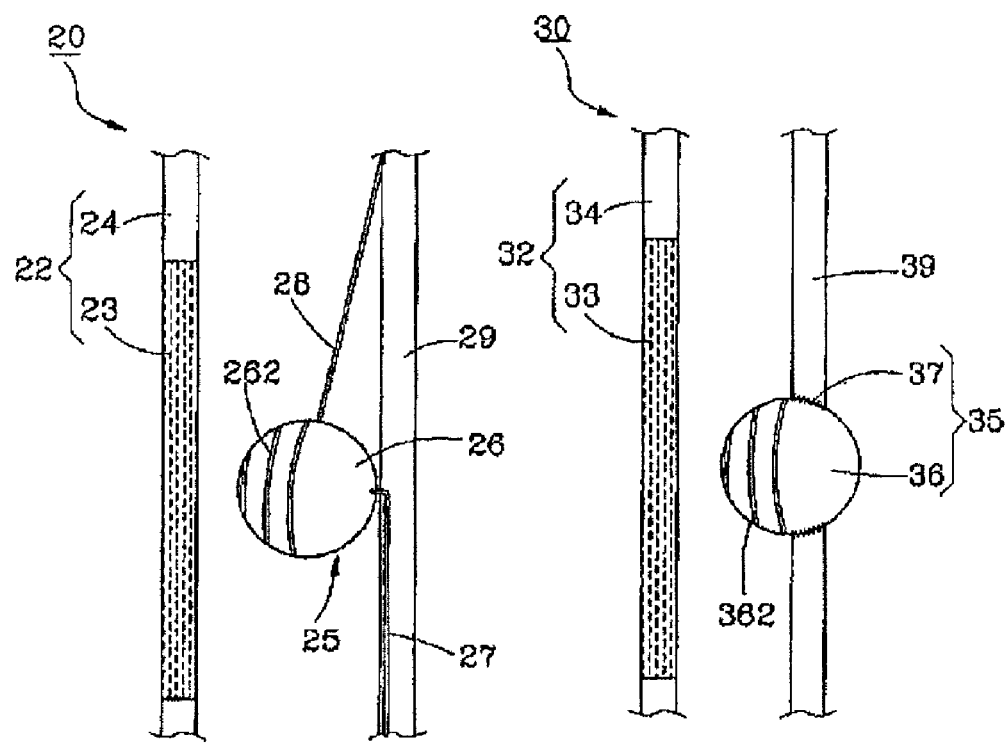
FIG. 12 shows a side view of this invention's eleventh preferred example.
FIG. 13 shows a side view of this invention's twelfth preferred example.

Please refer to FIG. 12, the cloth material 20 with separate conductive areas provided in this invention's eleventh preferred example includes a first layer 22, an extension part 25, a second layer 29, a control circuit (not shown), and an output device (not shown). The connecting part 27 of the extension part 25 is made of a metallic material, and it connects the accessory 26 and the second layer 29. The control circuit is also connected to the second conductive area 262 of the accessory 26 via the connecting part 27. In addition, the extension part 25 includes a non-conductive reinforcement wire 28 which is individually connected to the accessory 26 and the second layer 29, making the accessory 26 to be more securely fixed to the second layer 29. The reinforcement wire can incorporate an elastic material and have flexibility.

Please refer to FIG. 13, a cloth material 30 with separate conductive areas provided in this invention's twelfth preferred example is almost the same as that of the previous example. The only difference is that its accessory 36 is formed by sewing connecting wires 37 to the second layer 39. Similarly, when the first layer cloth material 30, which is nearest to the user's body, is pressed against the second layer of the accessory 36, a change in reaction may ne smaller than if the same force is applied on the second layer of the accessory 36 against the first layer cloth material 30 towards the user's body, because of behind the first layer cloth material 30 is the user's body. Therefore, the directions of force applied can be discerned.

Based on the above-mentioned structure, a manufacturer may use the first layer 32 and the second layer 39 to make a pair of under pants and a pair of trousers, respectively, to be worn by a user. The first and second conductive areas 33, 362 may be placed near the user's abdominal area. Based on this, the user can cause the first 33 and second conductive areas 362 to contact tightly by breathing deeply or tightening his abdominal wall, which causes the resistance level in the loop to decrease. Then, the output device may send a signal. Similarly, the control circuit may also cause the output device to send a signal by monitoring the change in capacitance level produced by the first 33 and second conductive areas 362. Furthermore, the first conductive area 33 may be designed to be ring-shaped so that the control circuit can command the output device to send a signal based on the reactive electromotive force formed in the first conductive area 33. When the first layer 32 is made into an undergarment, it can also act as an electrode. When the second layer is made into an outer garment, both the control circuit and the output device may be located on the outer garment. Therefore, it can read a user's ECG and change in respiration.

In addition, the first layer 32 can be designed into a chair, and the second layer 39 can be made into a shirt or a pair of pants for a user to wear. Based on this, the user can change his sitting position based on the correctness of the pressured part. The first layer 32 can also be designed into a surface of a bed sheet, and the second layer 39 can be made into a shirt or a pair of pants for the patient with chronic disease to wear. Through this, the caretaker can help turn the patient over at the proper time based on the location of the pressured part and the length of time that it has been under pressure, or know if the patient has fallen from his bed. In the beginning, the first and the second conductive areas may not conduct any current, unless compressed by an external force, as in lying down, where it becomes conductive. Therefore, this can save a lot of energy. Furthermore, the signals may be digital (instead of analog), avoiding the need for complicated signal processing.

Figure 14:
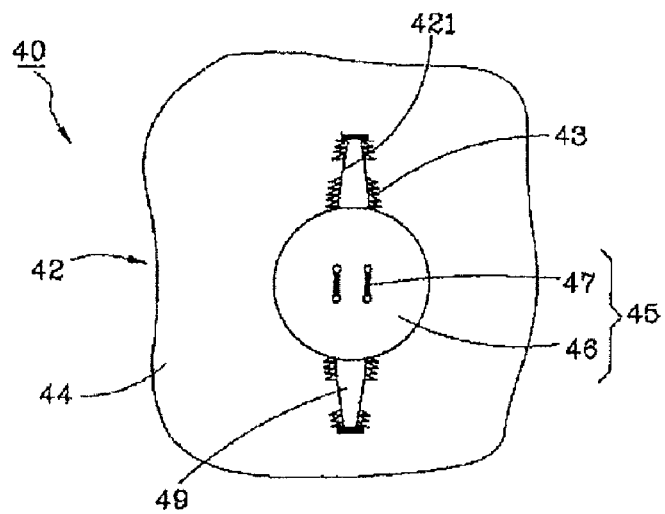
FIG. 14 shows a front view of this invention's thirteenth preferred example.

Based on the essence of this invention, the structure of a cloth material with separate conductive areas can have many variations. Now please refer to FIG. 14. A cloth material 40 with separate conductive areas provided in this invention's thirteenth preferred example similarly includes a first layer 42, an extension part 45, a second layer 49, a control circuit (not shown), and an output device (not shown). Both the first layer 42 and the second layer 49 may belong to ends of a single piece of cloth material. Like middle part of a shirt or cuffs of a suit, these two layers may be on two ends, one end containing the button, the other end containing the buttonhole. The first layer 42 may have a perforation 421, multiple conductive fine wires 43 and a non-sensor area 44. The conductive fine wires 43 are sewn along the perforation 421 and form the first conductive areas 43 on the first layer 42. The first conductive areas 43 (acting as the conductible fine wire 43 simultaneously) are separate from one another. The non-conductive area 44 is formed around the first conductive area 43. The extension part 45 has an accessory 46 and two connecting parts 47. The accessory 46 is in the form of a button and is made of an insulated material. It is sewn into the second layer 49 via the two connecting parts 47. The second layer 49 is made of an elastic material, such as a piece of elastic band, spandex, SBR, Styrene Butadiene Rubber, or a foam-based cotton material. The two connecting parts 47 are made of a conductive material, and they form the second conductive areas 47 of the extension part 45 (acting as the connecting part 47 simultaneously). The two connecting parts 47 also pass through the perforation 421 of the first layer 42. The first layer 42 is located between the accessory 46 and the second layer 49. Based on these, a user can pull and drag the first layer 42 and the second layer 49 in opposite direction, as in breathing or bending the wrist. The pulling or dragging is limited to the direction of the perforation 421, causing the second layer 49 to carry the button 46, to move along the perforation 421. Based on the connecting parts 47 coming into contact with the first conductive areas 43 at different locations, the control circuit can control the output device to send different signals. If the connecting part is made of a non-conductive material, while the button 46 is made of a conductive material, the button may replace the connecting part as the second conductive areas, which may achieve similar results. That is, the cloth material 40 with separate conductive areas may be used as a signal-producing device or as a strain gauge. For example, the first layer 42 may be a pair of pants, while the second layer 49 is a shoulder strap (a suspender). The buttons 46 are on the pants. Therefore, the changes in conduct of the user will cause similar changes in the second layer shoulder strap 49. Therefore, it can detect different digital signals produced by the first conductive area 43 and the second conductive area 47.

In addition, the circumference around the connecting parts 47 may be clad with an insulated material. Based on this, the control circuit can also cause the output device to send a signal by monitoring the changes in capacitance levels produced by the connecting parts 47 and the first conductive area 43.

Figure 15:
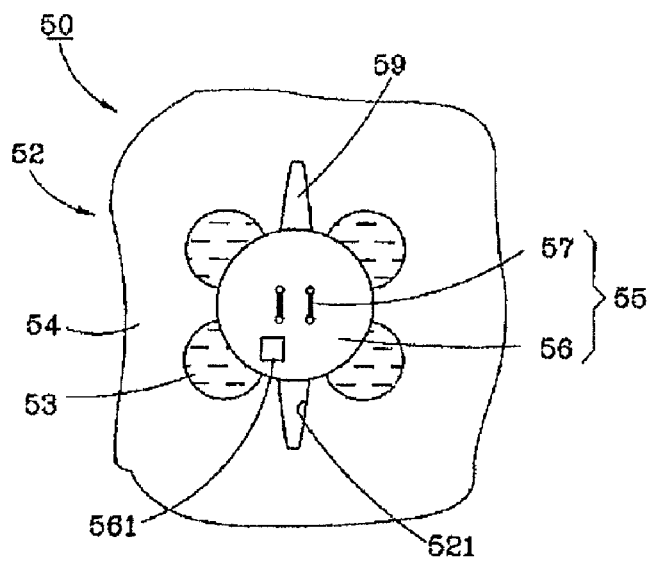
FIG. 15 shows a front view of this invention's fourteenth preferred example.

Now please refer to FIG. 15, a cloth material 50 with separate conductive areas provided in this invention's fourteenth preferred example is almost the same as that of the previous thirteenth example. They both include a first layer 52, a non-sensor area 54, an extension part 55, a second layer 59, a control circuit (not shown), and an output device (not shown). The only difference is that there are one or more independent first conductive areas 53 on the first layer 52, which may be round-shaped and separated from the rim of the perforation 521 by a pre-determined distance. The accessory 56 of the extension part 55 is made of a conductible material and is also in the form of a button 56 to form the second conductive area 56 of the extension part 55. The extension part 55 also includes an electronic part 561 located on the button 56, which is electrically connected to the connecting part 57. The electronic part 561 can include an integrated circuit (IC), a light emitting diode (LED), a sensor device, antenna, speakers, microphone, a resistor, a capacitor, an inductor or a battery.

A user can, as in breathing or swallowing, apply the pressure on the button 56 in order to tilt it and let it come into contact with the first conductive areas 53 on the first layer 52, forming a pressure detector, which can detect where the direction (up, down, left or right) of the pressure is coming from. Also, one can clad a layer of an insulated material on the bottom part of the button 56, for example plastic, so that the user can apply pressure on the button 56 to change the conductance values produced by the first and second conductive areas 53, 56.

Figure 16:
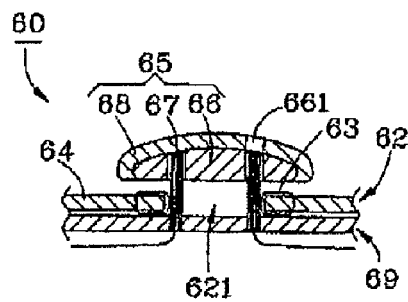
FIG. 16 shows a sectional view of this invention's fifteenth preferred example.

Now please refer to FIG. 16, a cloth material 60 with separate conductive areas provided in this invention's fifteenth preferred example is almost the same as that of the previous thirteenth example. The only difference is that the extension part 65 also includes a header 68 located in the accessory 66, and an electronic part 661 located in the header 68. The electronic part 661 is electrically connected to the connecting wire 67. The accessory 66 is made of a conductible material and is also in the form of a button 66. It also forms the second conductive area 66 of the extension part 65. The header 68 is made of an insulated material, thereby preventing accidental electrocution when the user touches the accessory 66.

Figure 17:
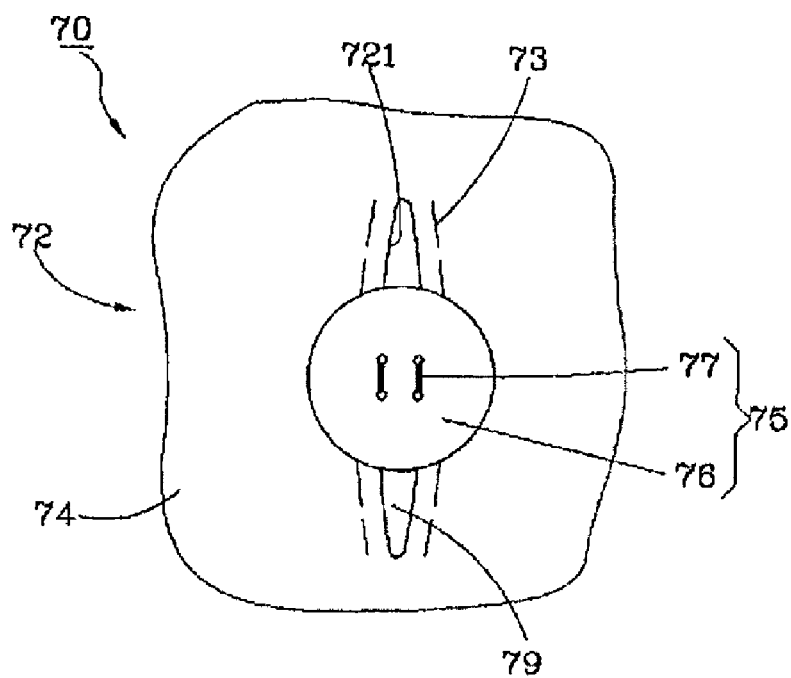
FIG. 17 shows a front view of this invention's sixteenth preferred example.

Now please refer to FIG. 17, a cloth material 70 with separate conductive areas provided in this invention's sixteenth preferred example is almost the same as that of the previous example. They both include a first layer 72, non-sensor area 74, an extension part 75, a second layer 79, a control circuit (not shown), and an output device (not shown). The first layer 72 has a perforation 721 and one first conductive area 73. Conductive fine wires are sewn along the perforation 721 to form the first conductive areas 73, at a location corresponding to the accessory 76; however, the two are not in contact with each other. The first conductive area is separated from the rim of the perforation 721 by a pre-determined distance. The connecting part 77 of the extension part 75 is made of a non-metallic material; the accessory 76 is made of a metallic material. When the second conductive area 76 is moved, the conductance values produced by the first and second conductive areas 73, 76 will change. The control circuit may then cause the output device to send a signal based on the changes in capacitance levels. The cloth material 70 with separate conductive areas that can automatically change its condition when external force is applied can be so designed that the first conductive area 73 forms at the rim of the perforation 721 of the first layer 72, and matches up with the outer part of the connecting part 77, which is clad with an insulated material and is the second conductive area.

Figure 18:
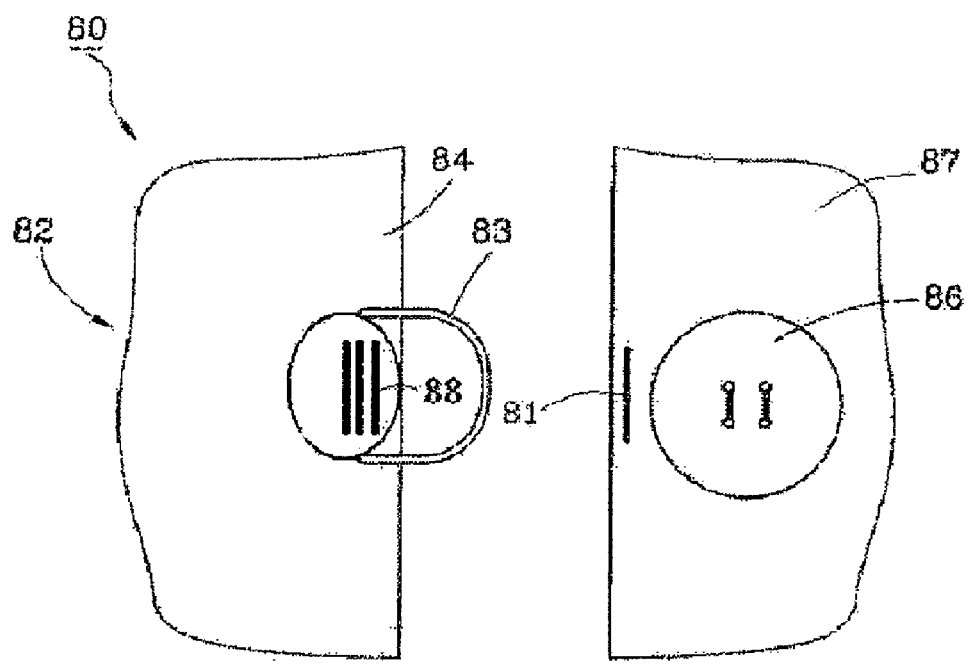
FIG. 18 shows a front view of this invention's seventeenth preferred example.

Please refer to FIG. 18, a cloth material 80 with separate conductive areas provided in this invention's seventeenth preferred example has the same non-conductive area 84, first layer 87, and a second layer 82 all located on the cloth layer 80. There is a first conductive area 81, a control circuit (not shown), and an output device (not shown) on the first layer 87. The only difference is that its second layer 82 has a ringed hook as the connecting part 83 which is elastic. The accessory 88 is sewn onto the second layer 82, forming the second conductive area. This accessory 88 is divided into three second conductive areas. There is button 86 on top of the first layer 87. Based on this, the ringed hook 83 can be put around the button 86. Different degrees of external force will produce different degrees of tension, causing the first conductive area to come into contact with the three different second conductive areas, thereby producing different signals. For example, if a user swallows or moves, he will cause a change in the accessory 88 and the first conductive area.

Figure 19:
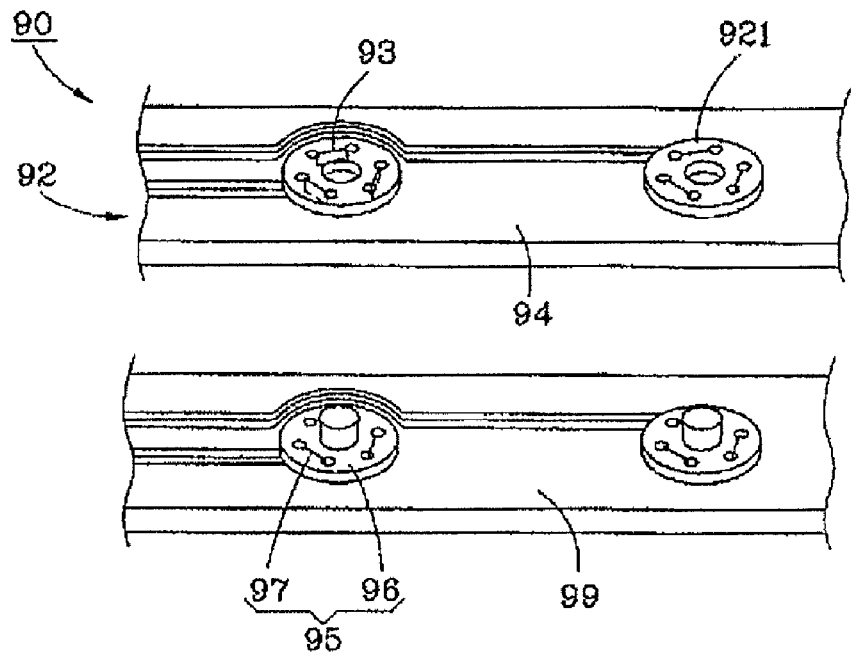
FIG. 19 shows a 3D view of this invention's eighteenth preferred example.

Please refer to FIG. 19, a cloth material 90 with separate conductive areas provided in this invention's eighteenth preferred example has the same one first layer 92, non-conductive area 94, two extension parts 95, one second layer 99, one control circuit (not shown), and an output device (not shown). The first layer 92 includes two female snap-on buttons 921, each being sewn onto the non-conductive area 94 using three conductive fine wires 93. The snap-on buttons 921 are made of an insulated material. The conductive fine wires 93 form three first conductive areas 93 (also functioning as conductive fine wires 93) of the first layer 92. The three conductive fine wires 93 can use other conductive material as substitute, and are electrically connected with the control circuit. The two extension parts 95 each contains one accessory 96 and three connecting part wires 97. The accessories 96 are sewn onto the second layer 99 via the extension parts 97. The accessories 96 are male snapped-on buttons and are made of an insulated material. The accessories 96 may separately be incorporated into the female buttons 921. The connecting parts 97 each form a second conductive area 97 (also functioning as a connecting part 97) of the extension part 95. Based on these, a user can button together a male portion 96 and a female portion 921 of the buttons, causing the first conductive areas 93 to come into contact with the second conductive areas 97, forming an electrical loop. Each pair of the male portion 96 and the female portion 921 of the buttons may conduct three different levels electrical currents or signals. Furthermore, the number of the male portions 96 and female portions 921 of the buttons may be one or more than three. The number of the male portions 96 of the buttons can be more than or less than that of the female portions 921.

Figure 20:
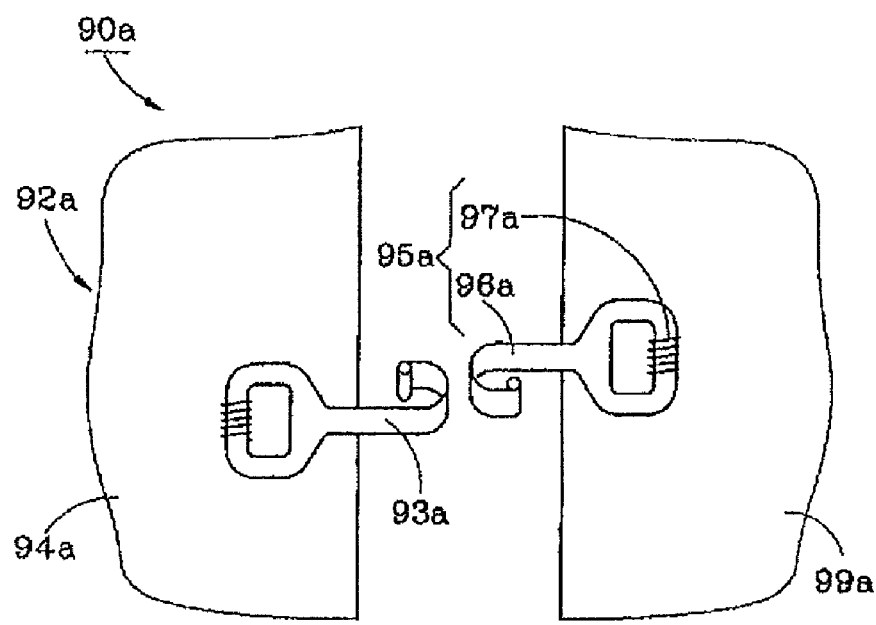
FIG. 20 shows a front view of this invention's nineteenth preferred example.

Please refer to FIG. 20, a cloth material 90a with separate conductive areas provided in this invention's nineteenth preferred example has the same one first layer 92a, one non-conductive area 94a, one extension parts 95a, one second layer 99a, one control circuit (not shown), and an output device (not shown). The first layer 92a has one clip hook 93a which is made of a conductive material and forms a first conductive area 93a on the first layer 92a. The extension part 95a has an accessory 96 that is sewn onto the second layer 99a using connecting wires. The accessory 96a is made of a conductive material and forms the second conductive area 96a (also functioning as the accessory 96a) of the extension part 95a. The connecting part 97a is made of a metallic material. Based on these, the clip hook 93a can be clipped onto the accessory 96a, forming an electrical loop.

Figure 21:
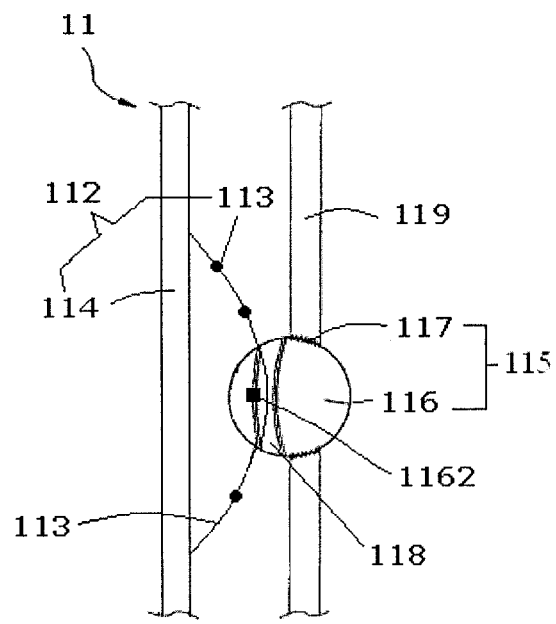
FIG. 21 shows a side view of this invention's twentieth preferred example.

Please refer to FIG. 21, a cloth material 11 with separate conductive areas provided in this invention's twentieth preferred example is almost the same as that of the twelfth example. The extension part 115 includes: an accessory 116 and a connecting part 117; the accessory is sewn onto the second layer 119 via the connecting part 117. The first layer cloth material 112 includes: a non-conductive area 114 and a first conductive area 113. The only difference is that the first conductive area 113 is composed of a wire-strip, and inside the accessory 116, there is a channel 118 that allows the first conductive area 113 to freely pass through. On the wire-strip, there are several first conductive areas. The accessory also has the second conductive areas 1162.

Based on the above structure, a manufacturer can individually make the first layer 112 and the second layer 119 into an upper garment and a sleeve for a user to wear, placing the first and second conductive areas 113,1162 near the armpit of the user. Based on this, the user can cause the first conductive area 113 and the second conductive area 1162 to be in close contact with each other by moving his upper arm, thereby lowering the resistance of the output device, and sending out signals. Similarly, the control circuit can also cause the output device to send out signals and sense the angle and speed of movement of the arm's movement by sensing the changes in the capacitance produced by the first conductive area 113 and the second conductive area 1162.

Figure 22:
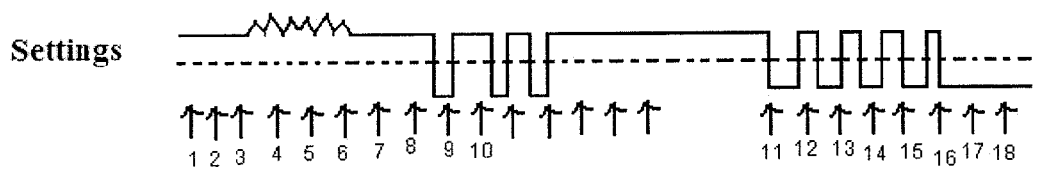
FIG. 22 shows a wave pattern of cloth material with separate conductive areas in accordance with one embodiment of the invention.
Figure 23:
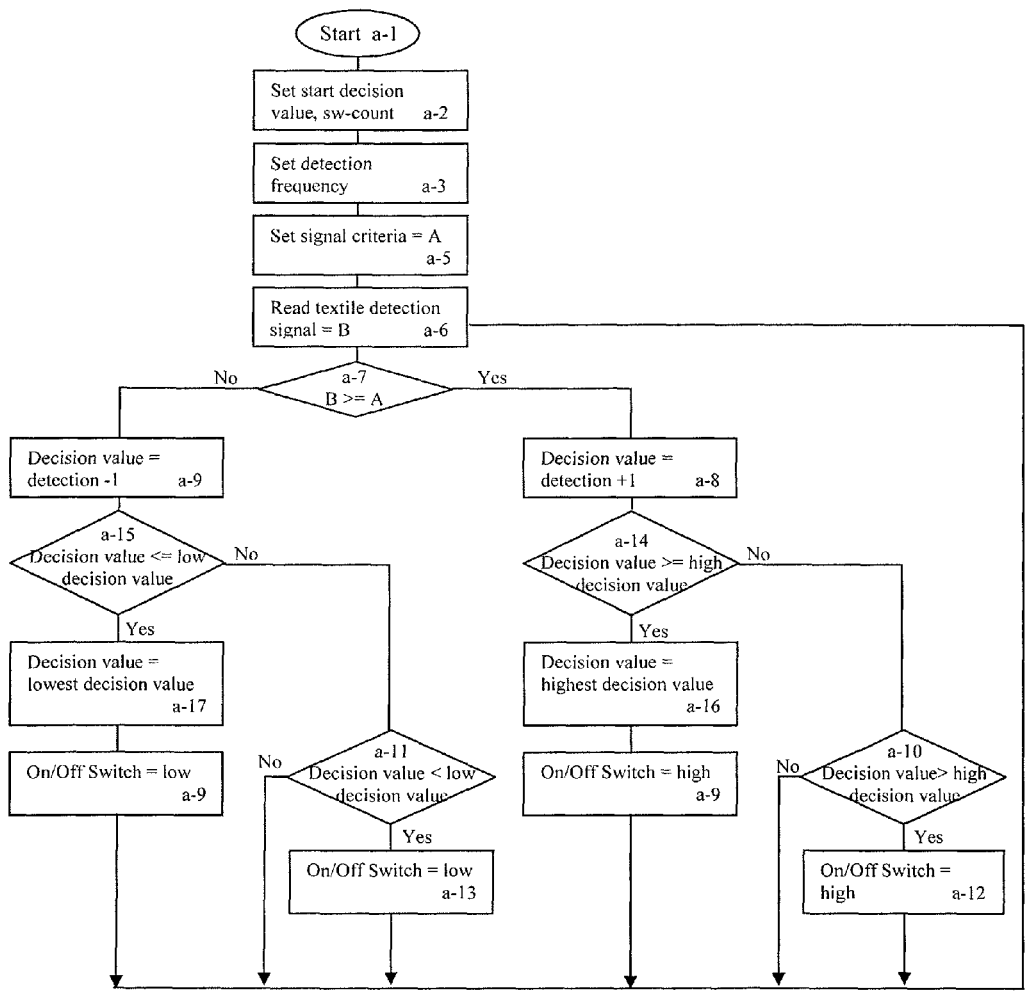
FIG. 23 shows a flow chart for processing oscillating signals of cloth material in accordance with one embodiment of the invention.

Please refer to FIG. 22. In accordance with the invention, cloth materials with separate conductive areas that can automatically change its condition when external force is applied work as follows:

When the first and the second conductive areas are influenced by an outside force, the change in sensing is illustrated in FIG. 22: the signals may have noise and may jump around. As shown in FIG. 23, the sensing process works like this: First one sets an initial determining value. In the absence of an outside force, the accessory and the cloth material area may be separated. It may be referred to as the "high" (or open) state. The "initial determining value" may be set to the highest or a high value. At the same time, the sampling rate is set, for example, once per second. Finally, one sets a "threshold value A" of the signal detector. For example, one may set the threshold values A to one-half the highest signal detected. Then, one starts to collect the signals detected by the accessories and the cloth materials at regular intervals as the "detected signal value B." If a "detected signal value B" is≧"threshold value A," then one adds 1 to the initial determining value, and at the same time initiates an evaluation process.

This evaluation will ascertain whether or not the "determining value" is the highest possible determining value expected. If it is the highest determining value or even higher, then the highest determining value is set as the "determining value." Then, one can conclude that the accessory and the cloth material are still not in contact with each other (in a high or open state). However, if the determining value is not the highest determining value, or does not exceed the highest determining value, then one assesses whether or not this determining value is higher than the expected determining value. If it is, then one concludes that the accessory and the cloth material are still not in contact with each other (still in a high or open state). If it is not, then one will repeat the evaluation process, using the determining value plus 1 as the "determining value."

If the "detected signal value B" is less than the "threshold value A," then 1 will be subtracted from the determining value, at the same time initiating an evaluation process. This evaluation will ascertain whether or not the "determining value" is the lowest possible determining value forecasted. If it is, the lowest value or even lower, then one will accept it as the "determining value." Then, one concludes that the accessory and the cloth material are in contact with each other (in a low or short state). However, if it is higher than the lowest determining value, then one will determine whether or not this determining value is lower than the forecasted low determining value. If it is, then one concludes that the accessory and the cloth material are in contact with each other (in a low or short state). If it is not, then one will repeat the evaluation process, using the determining value minus 1 as the "determining value."

Figure 24:
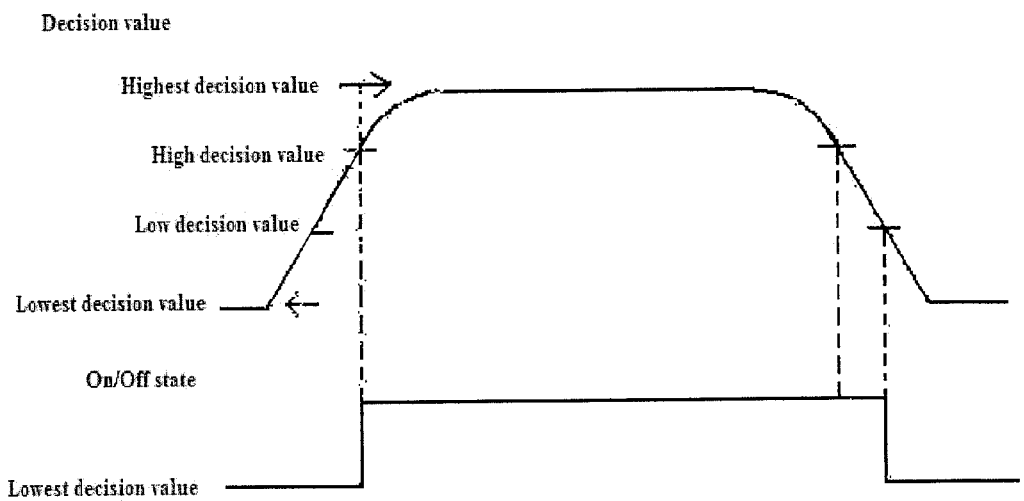
FIG. 24 shows an analytical diagram for processing the oscillating signals of a cloth material.

Explaining further, the determining factor of the wave form of the accessory and the cloth material is obtained by first getting the determining value after getting samples and putting it in the counter, as shown in FIG. 24, going over the boundary. And in the counter, there are the lowest determining value, low determining value, high determining value, and the highest determining value. Its wave form will be in between the lowest and the highest determining values, not lower than the lowest determining value and not higher than the highest determining value. When it reaches the highest determining value, we can ascertain that the accessory and the cloth material have been separated (in a high or open state). On the other hand, when it reaches the lowest determining value, we can ascertain that the accessory and the cloth material are in contact with each other (in a low or short state).

Figure 25:
FIG. 25 shows a practical wave pattern of the oscillating signals in FIG. 22 after signal processing with the Schmitt trigger algorithm.

Signals of FIG. 22, after processing the sense connection status using the method, are shown in FIG. 25. One can eliminate false signals and oscillating interference and obtain a standard which can be easily applied and completed, not needing any complicated calculations. It is an energy-saving, down-sized and wearable piece of innovation.

The above description clearly explains, with the aid of drawings, the advantages and applied examples of this invention. However, one skilled in the art would know that without extending beyond the scope of this invention, others can modify or change its model, even substituting other materials for its component parts. For example, for purposes of explaining, some embodiments of the invention have illustrated with a round-shaped accessory. However, one would understand that this can be substituted with other shapes of accessories. Therefore, the shapes of the conductive areas in the cloth materials should not limit the scope of this invention. Therefore, the invention is not restricted or limited to the preferred examples. Instead, this invention includes all examples that falls within the scope of its claimed rights.

On the basis of the essence of this invention, the structure of the cloth material equipped with separate conductive areas can have many variations. For example, the control circuit can be programmed with a time threshold (ex: 3 seconds). When the time of the electrical conduction between the first and second conductive areas exceeds the time threshold, the control circuit may command the output device to produce a signal, thereby preventing contact by mistake. Referring to the various changes of the above, the scope must be covered by this invention's patent application without exception.

INDUSTRIAL APPLICATION

This invention provides a type of cloth materials with separate conductive areas. These cloth materials can be incorporated into a user's cloth or leather apparel, including plastic and metallic accessories that can be worn by the user. It is easy to wear by a user and will not interfere with the user's body movements. It has the possibility of industrial utilization.

What is claimed is:

1. A cloth material with separate conductive areas, comprising:
   a first layer comprising a first conductive area; and
   an extension part, which includes an accessory and a connecting part connected to the accessory,
   wherein the extension part comprises a second conductive area, which corresponds in location to the first conductive area on the first layer,
   wherein the first conductive area and the second conductive area are inductively coupled, a condition of inductive coupling is adapted to be changed by an outside force.

2. The cloth material of claim 1, further comprising a control circuit connected with the first conductive area and the second conductive area.

3. The cloth material of claim 2, wherein the connecting part is connected to the first layer.

4. The cloth material of claim 1, further comprising at least one conductive reference area located on a layer of the cloth material.

5. The cloth material of claim 4, wherein the first conductive area, the second conductive area or the reference area is used as an electrode for ECG, a respiration sensor, EEG, EMG, moisture sensor, TENS device or a defibrillator.

6. The cloth material of claim 2, wherein the control circuit detects an induced electromotive force produced by the first or second conductive areas.

7. The cloth material of claim 1, wherein the first layer contains a perforation and wherein the first conductive area is formed in a periphery of the perforation, wherein the connecting part passes through the perforation.

8. The cloth material of claim 7, wherein the first conductive area is formed along a rim of the perforation, and separated from the rim of the perforation by a pre-determined distance, wherein the connecting part passes through the perforation.

9. The cloth material of claim 4, wherein the reference area comprises two or more reference areas electrically connected with the control circuit, wherein the control circuit is capable of detecting an electrical leakage based on whether there is an electrical loop existing between the two or more reference areas.

10. The cloth material of claim 3, wherein the control circuit includes either an ohmmeter or capacitance meter.

11. The cloth material of claim 1, wherein the accessory of the extension part is either spherical, cylindrical, ring-shaped, long strip, button, sequin, bead or cone in shape where there is a fillister side or a protruding side.

12. The cloth material of claim 1, wherein the first conductive area is used as a signal or electric current transmitter.

13. The cloth material of claim 1, wherein the second conductive area is made of a conductive material, a magnetic material, or an electromagnetic material.

14. The cloth material of claim 1, wherein the extension part includes an electronic component located in the accessory, wherein the electronic component is electrically connected with the connecting part, wherein the electronic component is selected from an integrated circuit (IC), a light emitting diode (LED), a sensor device, an antenna, a speaker, a microphone, a resistor, a capacitor, an inductor, or a battery.

15. The cloth material of claim 1, wherein a change in the inductive coupling produced by the outside force applied is in a form of a digital change.

16. The cloth material of claim 1, wherein the cloth material is configured for use as a switch matrix, a keyboard, a pressure gauge, a strain gauge, a signal-producing device, an electric current-producing device, a detector of position or gait change, a breathing monitor, a heartbeat monitor, a swallowing sensor, a resistor, an inductor, a position change detector, a speedometer, an acceleration detector, a capacitor, a variable resistor, a variable capacitor, a variable inductor, or a switch.

17. The cloth material of claim 1, further comprising a second layer, wherein the connecting part is connected with the second layer, wherein a distance between the first conductive area and the second conductive area changes with an outside force.

18. The cloth material of claim 17, wherein the first layer is located between the second layer and a clothing or garment.

* * * * *